(12) United States Patent
Roenspies et al.

(10) Patent No.: US 9,902,414 B2
(45) Date of Patent: Feb. 27, 2018

(54) LOCOMOTIVE INCLUDING OPERATOR FATIGUE MONITORING SYSTEM

(71) Applicant: Electro-Motive Diesel, Inc., LaGrange, IL (US)

(72) Inventors: David Matthew Roenspies, Elburn, IL (US); James David Seaton, Westmont, IL (US); Alex Shubs, Chicago, IL (US)

(73) Assignee: Electro-Motive Diesel, Inc, LaGrange, IL (US)

( * ) Notice: Subject to any disclaimer, the term of this patent is extended or adjusted under 35 U.S.C. 154(b) by 63 days.

(21) Appl. No.: 15/047,255

(22) Filed: Feb. 18, 2016

(65) Prior Publication Data

US 2017/0240192 A1    Aug. 24, 2017

(51) Int. Cl.

| | |
|---|---|
| *B61L 27/04* | (2006.01) |
| *A61B 5/18* | (2006.01) |
| *B61C 3/00* | (2006.01) |
| *B61L 15/00* | (2006.01) |
| *B60T 7/14* | (2006.01) |
| *B60T 13/66* | (2006.01) |
| *B60T 17/22* | (2006.01) |
| *A61B 10/00* | (2006.01) |
| *A61B 5/0205* | (2006.01) |

(52) U.S. Cl.
CPC ............... *B61L 27/04* (2013.01); *A61B 5/18* (2013.01); *B60T 7/14* (2013.01); *B60T 13/665* (2013.01); *B60T 17/228* (2013.01); *B61C 3/00* (2013.01); *B61L 15/00* (2013.01); *A61B 5/0205* (2013.01); *A61B 2010/0009* (2013.01); *A61B 2503/22* (2013.01)

(58) Field of Classification Search
CPC .............. B61L 27/04; B61C 3/00; A61B 5/18
USPC .................. 701/20; 340/425.5; 600/300, 529
See application file for complete search history.

(56) References Cited

U.S. PATENT DOCUMENTS

| | | | |
|---|---|---|---|
| 6,822,573 | B2 | 11/2004 | Basir et al. |
| 6,927,694 | B1 | 8/2005 | Smith et al. |
| 8,725,311 | B1 | 5/2014 | Breed |
| 8,981,942 | B2 | 3/2015 | He et al. |
| 2011/0043350 | A1* | 2/2011 | Ben David .............. B60Q 9/00 340/441 |

(Continued)

FOREIGN PATENT DOCUMENTS

CN    100462046 C    2/2009

*Primary Examiner* — Tan Q Nguyen
(74) *Attorney, Agent, or Firm* — Miller, Matthias & Hull

(57) ABSTRACT

A locomotive is disclosed. The locomotive includes a car body, including an operator cabin, a power source, and an operator health monitor within the operator cabin, the operator health monitor configured to monitor at least one health condition associated with the operator and configured to generate an operator health signal associated with the at least one condition. The locomotive includes an operator warning system within the operator cabin, configured to present the operator with an operator warning in response to an operator warning signal, and an electronic controller. The electronic controller may be configured to determine an operator fatigue score based on, at least, the operator health signal, determine if the operator fatigue score exceeds a warning threshold, and transmit the operator warning signal to the operator warning system if the operator fatigue score exceeds the warning threshold.

17 Claims, 5 Drawing Sheets

(56) References Cited

U.S. PATENT DOCUMENTS

2014/0167967 A1* 6/2014 He .......................... B60Q 9/00
340/576
2015/0284653 A1* 10/2015 Shmyreva ............ C10M 103/06
508/108
2016/0311440 A1* 10/2016 Gan ....................... B60K 28/06

* cited by examiner

LOCOMOTIVE INCLUDING OPERATOR FATIGUE MONITORING SYSTEM

RELATED APPLICATIONS

This application is related to U.S. patent application Ser. No. 14/820,281 filed on Aug. 6, 2015, the contents of which are expressly incorporated herein by reference.

TECHNICAL FIELD

The present disclosure generally relates to locomotive transportation systems and devices and, more particularly, to locomotives utilizing operator fatigue monitoring systems.

BACKGROUND

While operating a locomotive, operators can become fatigued after extended periods in which they control the locomotive. In some locomotives, repetitive motions are required, which may tire the operator. Alternatively, some locomotives may require very little operator movement, which can result in operator drowsiness. In either situation, the operator's concentration may be impaired and/or his/her attentiveness may wane. Such a dulling of concentration or attentiveness may result in improper machine control, delayed machine control, or a lack of machine control.

In order to combat operator fatigue in locomotives, systems and methods for alerting the operator and/or combating fatigue are used. Such systems may monitor locomotive operations and/or operations of the user and subsequently provide feedback to the operator based on the monitoring. Operator fatigue monitoring systems may observe visual characteristics of the operator or they may evaluate operator fatigue based on operator input to the locomotive controls. However, over time, the operator can become accustomed to providing such repetitive input and, thusly, this may not fully evaluate operator fatigue.

To combat this issue, further developments have been made in operator fatigue monitoring and alerting systems, such as the systems and methods described in U.S. patent application Ser. No. 14/820,281 ("Operator Fatigue Monitoring System"). The '281 application discloses systems and methods for monitoring fatigue of an operator of a machine, wherein scanning devices are used to scan for recognized characteristics of the operator (e.g., facial indications associated with fatigue). If fatigue is detected based on input from the scanning devices, warnings may be made to the operator or braking of the machine may commence.

While the systems and methods of the '281 application do present advances in operator fatigue monitoring, additional components may be utilized to more accurately detect fatigue in a locomotive operator. Therefore, locomotives utilizing systems and methods for operator fatigue monitoring, which include input from an operator health monitoring device, are desired.

SUMMARY

In accordance with one aspect of the disclosure, a locomotive is disclosed. The locomotive is operated by an operator and configured to move along a track. The locomotive may include a car body including an operator cabin and a power source for generating electricity for the locomotive. The locomotive may further include an operator health monitor within the operator cabin, the operator health monitor configured to monitor at least one health condition associated with the operator and configured to generate an operator health signal associated with the at least one condition. The locomotive may further include an operator warning system within the operator cabin configured to present the operator with an operator warning in response to an operator warning signal and an electronic controller operatively associated with the operator health monitor and the operator warning system. The electronic controller may be configured to receive the operator health signal, determine an operator fatigue score based on, at least, the operator health signal, determine if the operator fatigue score exceeds a warning threshold, and transmit the operator warning signal to the operator warning system if the operator fatigue score exceeds the warning threshold.

In accordance with another aspect of the disclosure, a system for monitoring fatigue of an operator of a locomotive is disclosed. The locomotive may include a car body having an operator cabin. The system may include an operator health monitor within the operator cabin, the operator health monitor configured to monitor at least one health condition associated with the operator and configured to generate an operator health signal associated with the at least one condition. The system may further include an operator warning device configured to present the operator with an operator warning in response to an operator warning signal and a controller operatively associated with, at least, the operator health monitor. The controller may be configured to receive the operator health signal, determine an operator fatigue score based on, at least, the operator health signal, determine if the operator fatigue score exceeds a warning threshold, and transmit the operator warning signal to the operator warning signal if the operator fatigue score exceeds the warning threshold.

In accordance with yet another aspect of the disclosure, a method for monitoring fatigue of an operator of a locomotive is disclosed. The method may include monitoring at least one health condition of the operator and generating an operator health signal associated with the at least one condition, by an operator health monitor within an operator cabin of the locomotive. The method may further include receiving the operator health signal, determining an operator fatigue score based on, at least, the operator health signal and determining if the operator fatigue score exceeds a warning threshold, by an electronic controller. The method may further include presenting the operator with an operator warning if the operator fatigue score exceeds the warning threshold.

These and other aspects and features of the present disclosure will be better understood when read in conjunction with the accompanying drawings.

While the following detailed description will be given with respect to certain illustrative embodiments, it should be understood that the drawings are not necessarily to scale and the disclosed embodiments are sometimes illustrated diagrammatically and in partial views. In addition, in certain instances, details which are not necessary for an understanding of the disclosed subject matter or which render other details too difficult to perceive may have been omitted. It should therefore be understood that this disclosure is not limited to the particular embodiments disclosed and illustrated herein, but rather to a fair reading of the entire disclosure and claims, as well as any equivalents thereto.

DETAILED DESCRIPTION

Figure 1:
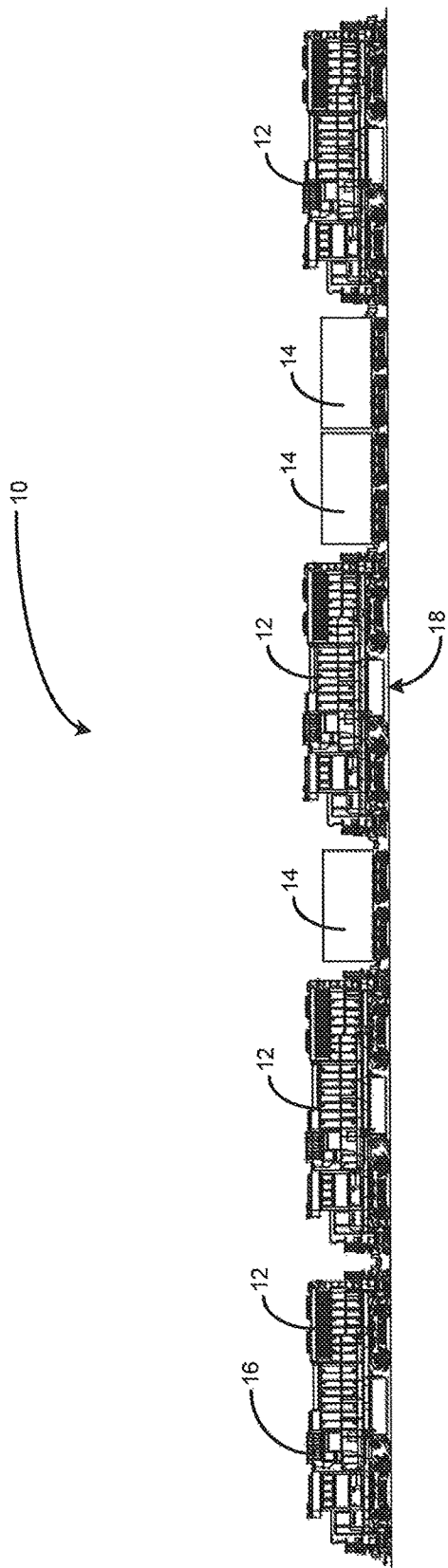
FIG. 1 is a side view of an exemplary train, in accordance with the present disclosure.

Referring now to the drawings and with specific reference to FIG. 1, an exemplary train 10 is shown. The train 10 may include one or more locomotives 12 coupled with one or more railcars 14. In some example configurations, the one or more locomotives 12 may include a lead locomotive 16, at the front of the train 10, and the train 10 may be configured such that the lead locomotive 16 is coupled with other locomotives 12 and the one or more railcars 14. As a result, control commands made in the lead locomotive 16 may be transmitted directly or indirectly to the other locomotives 12 and the railcars 14. Such a train 10 that includes one or more locomotives 12 communicatively coupled with one or more railcars 14 and configured to propel the train 10 down a track 18 may be referred to as a consist.

Figure 2:
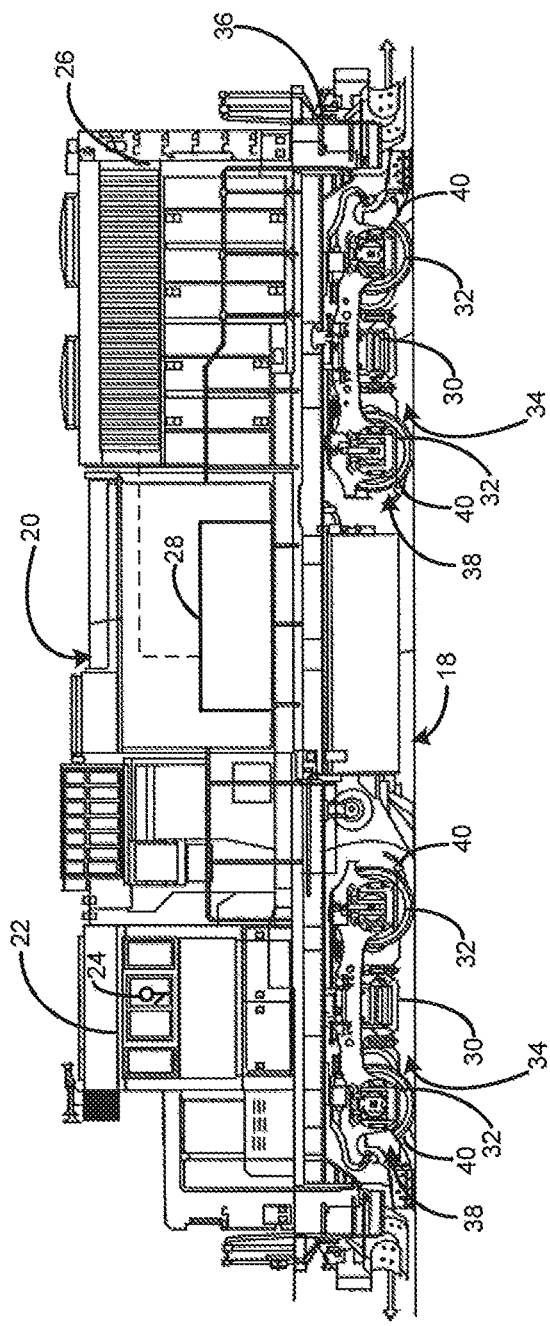
FIG. 2 is a side view of a locomotive including a cabin, within which an operator may operate and/or control the locomotive, in accordance with the present disclosure.

Turning now to FIG. 2 and with continued reference to FIG. 1, an example locomotive 12, including a car body 20, is illustrated. The car body 20 may include an operator cabin 22, wherein an operator 24 may control operations of the locomotive 12 and/or the train 10 at large. The locomotive 12 may include an engine 26 coupled with a generator 28, or other power source, located on the locomotive 12. The engine 26 may be a diesel, steam, gas turbine, electric, hybrid, or any other known type of engine capable of generating electricity for the locomotive 22. The generator 28 may be driven by the engine 26 in order to produce electricity that is used to propel the locomotive 12, and any associated railcars 14, along the track 18. For example, the electricity produced by the generator 28 may be used by one or more traction motors 30 that are configured to drive one or more wheels 32 attached to the locomotive 12.

The generator 28 may also provide electricity for other systems, such as control systems, status systems or any other system that consumes electricity during the operation of the train 10. The traction motors 30 and wheels 32 may be coupled to the locomotive 12 using a chassis or subassembly often referred to as a bogie 34 or truck. In some embodiments, the locomotive 12 may have a plurality of bogies 34, each configured with a traction motor 30 and two sets of wheels 32; however, other configurations are certainly possible. Moreover, the bogies 34 may include other components such as brakes, axles (not shown) or any other components associated with the bogies 34. The bogies 34 may be attached to a locomotive frame 36 and the frame 36 may be further configured to support the car body 20, the engine 26, the generator 28 and any other locomotive 12 components associated with the locomotive 12. A braking system 38 may be provided, including one or more braking devices 40. The one or more braking devices 40 may each be associated with one or all wheels 32 of a particular bogie 34. Control over wheel braking and engine fueling (as well as other locomotive controls) may be performed using one or more devices found within the operator cabin 22.

Figure 3:
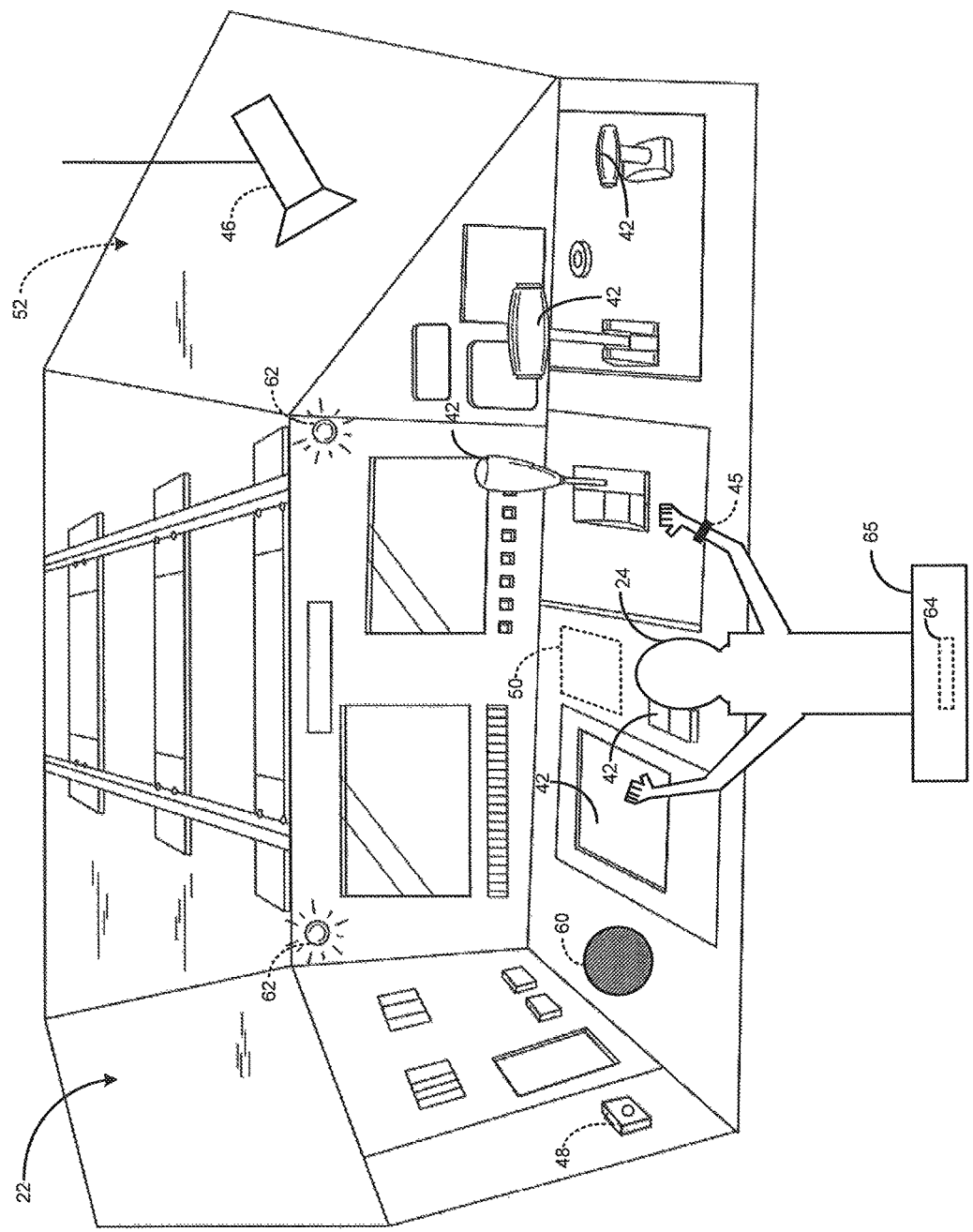
FIG. 3 is an isometric illustration of an interior of the cabin of the locomotive of FIG. 2, including an operator fatigue monitoring system, in accordance with an embodiment of the present disclosure.

Turning now to FIG. 3 and with continued reference to FIG. 2, the interior of the exemplary operator cabin 22 is shown. As shown, the operator cabin 22 may house a plurality of input devices 42, which may be used by the operator 24 to control the locomotive 12 and may include any input device known in the art. For example, input devices 42 may include, among other things, a throttle configured to control fueling of locomotive 12 and a brake lever configured to control braking of locomotive 12 via the braking system 38. Input devices 42 may be levers, pedals, wheels, knobs, push-pull devices, touch screen displays, and the like.

Figure 4:
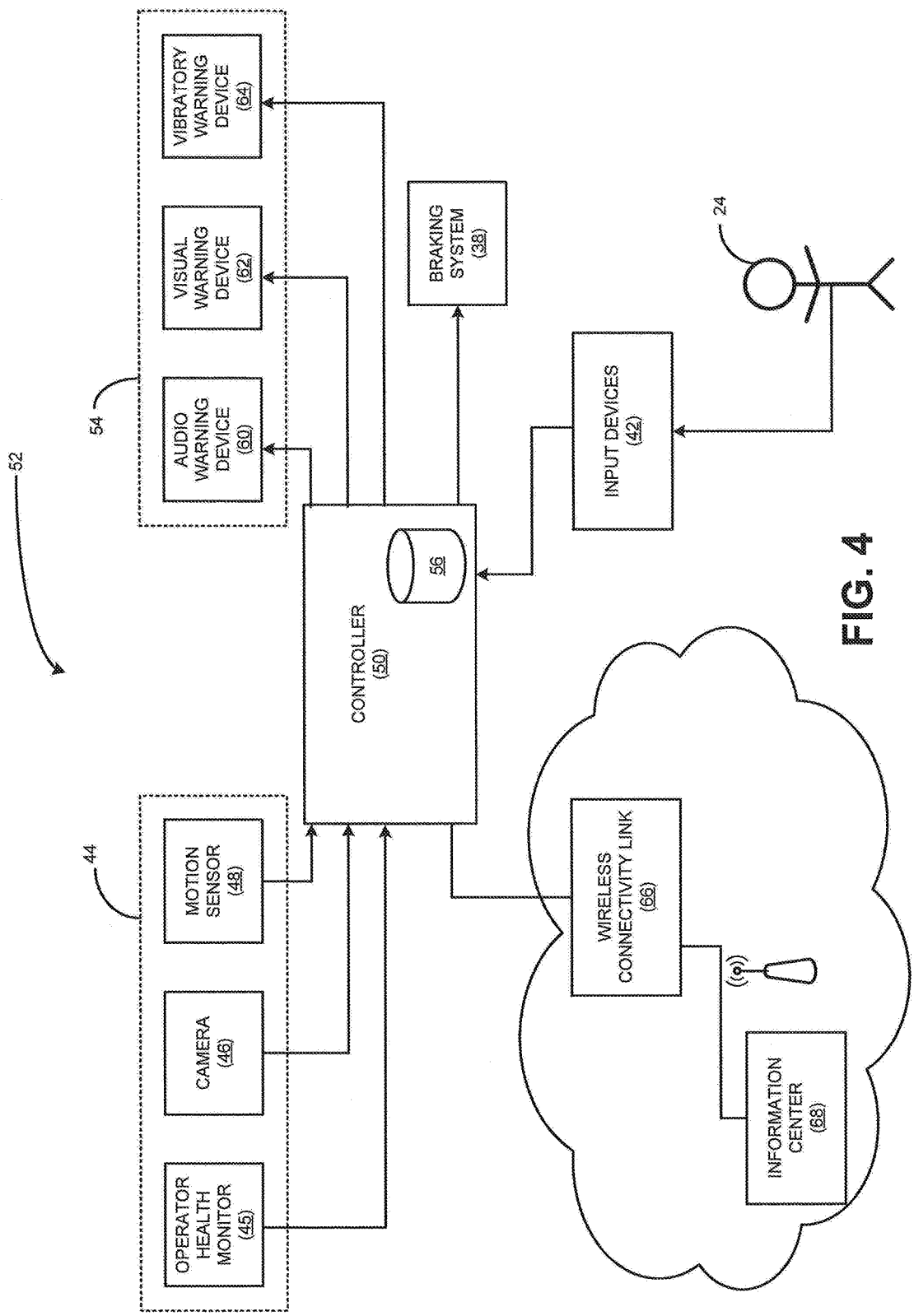
FIG. 4 is a schematic diagram of the operator fatigue monitoring system of FIG. 3, in accordance with FIG. 3 and the present disclosure.

A variety of monitoring devices 44 may be used, alone or in conjunction, to monitor operator movement, operator fatigue, or any other physical or mental conditions associated with the operator 24. The monitoring devices 44 may include, but are not limited to including, an operator health monitor 45, visual sensors, such as a camera 46, and a motion sensor 48. Such devices may be utilized, as illustrated graphically in FIG. 3 and depicted schematically in FIG. 4, in operative association with a controller 50, as part of an operator fatigue monitoring system 52.

For example, the operator fatigue monitoring system 52 may utilize the operator health monitor 45 to monitor one or more health conditions associated with the operator 24 and generate an operator health signal associated with the one or more health conditions associated with the operator 24. Such health conditions to be monitored may include, but are not limited to including, a body temperature of the operator 24, blood alcohol content (BAC) of the operator 24, heart rate of the operator 24, blood pressure of the operator 24 and/or any other health condition of the operator 24. To gather such information from the operator 24, the operator health monitor 45 may include, but is not limited to including, a heart rate monitor, galvanic skin response sensors, BAC monitors, sweat analyzing sensors, blood pressure monitors, and the like.

In some examples, such as the example embodiment of FIG. 3, the operator health monitor 45 may be a wearable operator health monitor 45, which is worn by the operator 24 during operation of the locomotive 12. Such a wearable operator health monitor 45 may include any of the aforementioned health tracking devices described above and may further include additional or alternative health tracking devices. Further, in a non-limiting example, the wearable operator health monitor 45 may be embodied by a fitness tracking device which communicates with the controller 50. Such fitness tracking devices, which may be utilized to embody the wearable operator health monitor 45, may include commercially available fitness trackers (e.g., FitBit® fitness trackers, Jawbone UP® fitness trackers, Nike+® trackers, and the like) and/or fitness tracking devices designed specifically for use as the wearable operator health monitor 45.

In addition to gathering fatigue-related information from the operator health monitor 45, the operator fatigue monitoring system 52 may further utilize the camera 46 and the motion sensor 48 to gather additional data associated with fatigue levels of the operator 24. The camera 46 may be disposed in the cabin 22 and configured to generate visual operator fatigue signals, based on visual monitoring of the operator 24. For example, the visual operator signals may detect, or may be processed, by the controller 50, to detect, motion of the operator 24 indicative of fatigue, facial characteristics of the operator 24 which are indicative of fatigue, eye conditions of the operator 24 that are indicative of fatigue, and/or any other visual characteristics of the operator 24 that may indicate fatigue. Further, the motion sensor 48 may be configured to generate an operator motion signal, which may be indicative of whether or not a lack of motion by the operator 24 exists. Such a lack of motion may be indicative of fatigue in the operator 24.

The operator fatigue monitoring system 52 may utilize the signals generated by the monitoring devices 44 to determine fatigue in the operator 24 and potentially take corrective action via an operator warning system 54 or the braking system 38. Evaluation of one or more of the operator health signal, the visual operator fatigue signal, and the operator motion signal to determine the operator fatigue may be executed by the controller 50.

The controller 50 may be any electronic controller or computing system including a processor which operates to perform operations, execute control algorithms, store data, retrieve data, gather data, and/or any other computing or controlling task desired. The controller 50 may be a single controller or may include more than one controller disposed to control various functions and/or features of the operator fatigue monitoring system 52 and/or the locomotive 12. Functionality of the controller 50 may be implemented in hardware and/or software and may rely on one or more data maps relating to the operation of the operator fatigue monitoring system 52 and/or the locomotive 12. To that end, the controller 50 may include internal memory 56 and/or the controller 50 may be otherwise connected to external memory, such as a database or server. The internal memory 56 and/or external memory may include, but are not limited to including, one or more of read only memory (ROM), random access memory (RAM), a portable memory, and the like. Such memory media are examples of nontransitory memory media.

In operation, the controller 50 may be configured to receive the operator health signals from the operator health monitor 45. Additionally, the controller 50 may receive the visual operator fatigue signals from the camera 46 and/or may receive the operator motion signals from the motion sensor 48. Utilizing the operator health signals and, optionally, one or both of the visual operator fatigue signals and the operator motion signals, the controller 50 may determine an operator fatigue score based on said selected signals. The operator fatigue score may be a calculation of known signs of fatigue recognized from the input signals, wherein a given score may be evaluated versus one or more thresholds to determine if, based on the score, the operator fatigue system 52 should take corrective action.

In a non-limiting example, the controller 50 may evaluate the operator fatigue score based on a plurality of thresholds. For example, the controller 50 may determine if the operator is fatigued at a first threshold, at a second threshold, or at a third threshold. Of course, any number of thresholds corresponding with any number of operator fatigue scores are certainly possible. In the present example, the first threshold may be associated with a score representative of slightly fatigued operator wherein response time and/or judgment may be somewhat impaired. In instances wherein the operator fatigue score exceeds the first threshold, an operator warning signal may be transmitted to the operator warning system 54, by the controller 50, so that the operator may be alerted and brought out of the fatigued state. The second threshold may be associated with an operator fatigue score representative of a significantly fatigued operator wherein response time and/or judgment is significantly impaired. In such instances, the controller 50 may transmit an operator warning signal to the operator warning system 54 and/or the controller 50 may direct the braking system 38 to slow speed of the locomotive 12. Further, the third threshold may be associated with an operator fatigue score which may correspond with an unresponsive operator (e.g., an operator that has fallen asleep). In these instances, the controller 50 may transmit an operator warning signal to the operator warning system 54, the controller 50 may direct the braking system 38 to slow speed of the locomotive 12, and/or the controller 50 may direct the braking system 38 to halt motion of the locomotive 12. It is contemplated that any number of fatigue thresholds, such as those corresponding to a need for a warning or a need for braking, may be utilized by system 52, and/or that the thresholds for fatigue may have different meanings, if desired.

The operator warning system 54 may include a plurality of operator warning devices including, but not limited to, an audio warning device 60, a visual warning device 62, and a vibratory warning device 64. The audio warning device 60 may be any audio device capable of providing an audible signal to the operator 24 like, for example, a speaker. Such audible signals may be any audible noise of any amplitude, configured to alert the operator 24, in response to an operator warning signal from the controller 50. The visual warning device 62 may be any lights, screens, or any visual device which may be configured to provide the operator 24 with any form of visual stimuli, in response to an operator warning signal from the controller 50. Further, the vibratory warning device 64 may be any vibratory and/or haptic device configured to alert the operator 24 via one or more vibrations, in response to an operator warning signal. As shown in FIG. 3, the vibratory warning device 64 may be embedded in, or otherwise associated with, a seat 65 used by the operator 24, such that the vibratory warning device 64 will provide a vibratory warning to the operator 24 via the seat 65. Of course, the vibratory warning device 64 may located anywhere within the cabin 22, wherein vibratory signals from the device will reach the operator 24.

In some examples of the operator fatigue monitoring system 52, the system 52 may include a wireless connectivity link 66 operatively associated with the controller 50. The wireless connectivity link 66 may be configured to transmit operator fatigue scores, or any other fatigue information associated with the operator 24, to an information center 68 associated with the locomotive 12. Such transmissions may occur over any wireless network, such as, but not limited to, a wireless long area network (WLAN), WiFi network, or a cellular data network.

INDUSTRIAL APPLICABILITY

In general, the present disclosure may find applicability in many industries, for example locomotives and the rail industry. In that regard, the present disclosure generally relates to locomotive transportation systems and devices and, more particularly, to locomotives utilizing operator fatigue monitoring systems. The disclosed locomotives, systems, and methods may be utilized to provide alerting capabilities to locomotives and to enhance operator interactivity with the locomotive. Further, the disclosed systems and methods may improve concentration or attentiveness of locomotive operators. By utilizing the operator health monitor 45, disclosed herein, the operator fatigue monitoring system 52 of the present disclosure may gain greater insight into a fatigued state of the operator, with respect to prior art fatigue monitoring systems.

Figure 5:
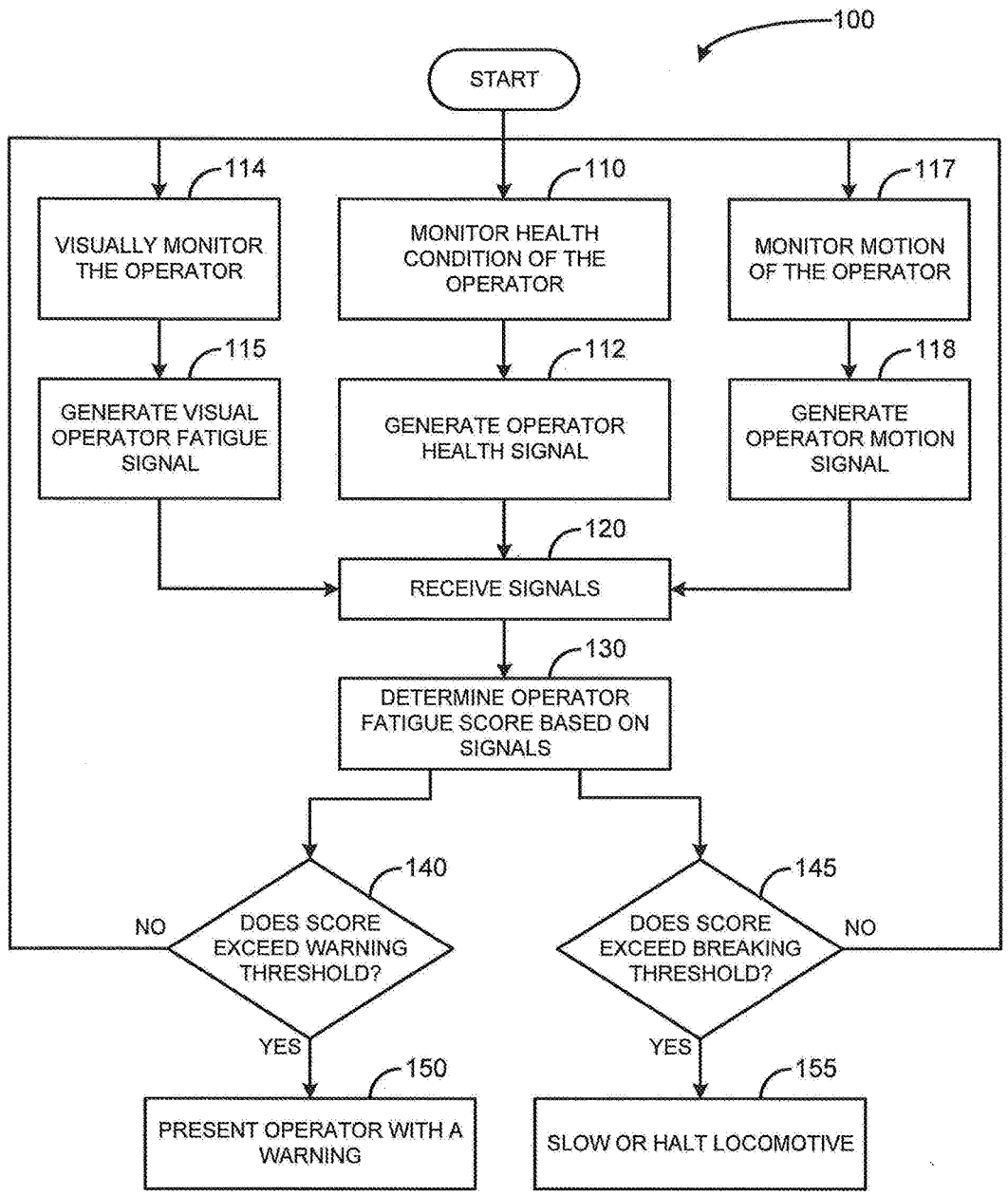
FIG. 5 is a flow chart representative of a method for monitoring operator fatigue in a locomotive, in accordance with the present disclosure.

To that end, a method 100 for monitoring operator fatigue, which utilizes the operator health monitor 45, is illustrated in the block diagram of FIG. 5. The method 100 begins at block 110, wherein the operator health monitor 45 monitors at least one health condition of the operator 24, as described above, and then, at block 112, an operator health signal is generated by the operator health monitor 45, based on the at least one health condition. Concurrently, prior to, or after blocks 110 and 112, the method 100 may include visually monitoring the operator 24, utilizing the camera 46, as shown in block 114 and/or the method 100 may include monitoring motion of the operator 24 with the motion sensor 48, as shown in block 117. Following block 114, the method 100 may continue to block 115 wherein the visual operator fatigue signal is generated. Similarly, following block 117, the method 100 may continue to block 118, wherein the operator motion signal is generated.

At block 120, the controller 50 receives the operator health signal and, optionally, one or both of the operator motion signal and the visual operator fatigue signal. Using the received signals, the controller 50 determines an operator fatigue score based on said signals, as shown in block 130. At decision 140, the controller 50 determines if the operator fatigue score exceeds an operator warning threshold. If the operator fatigue score indeed exceeds the operator warning threshold, then the method continues to block 150, wherein the controller 50 transmits an operator warning signal to the operator warning system 54, which presents a warning to the operator 24. Similarly, at decision 145, the controller 50 determines if the operator fatigue score exceeds breaking threshold and, if the score does exceed such a threshold, the controller 50 directs the braking system 38 to slow or halt motion of the locomotive, as shown in block 155.

It will be appreciated that the present disclosure provides locomotives, in addition to associated systems and methods, which utilize operator fatigue monitoring systems. While only certain embodiments have been set forth, alternatives and modifications will be apparent from the above description to those skilled in the art. These and other alternatives are considered equivalents and within the spirit and scope of this disclosure and the appended claims.

What is claimed is:

1. A locomotive operated by an operator and configured to move along a track, the locomotive comprising:
   a car body including an operator cabin;
   a power source for generating electricity for the locomotive;
   an operator health monitor within the operator cabin, the operator health monitor configured to monitor at least one health condition associated with the operator and configured to generate an operator health signal associated with the at least one condition;
   an operator warning system within the operator cabin configured to present the operator with an operator warning in response to an operator warning signal;
   an electronic controller operatively associated with the operator health monitor and the operator warning system, the controller configured to receive the operator health signal, determine an operator fatigue score based on, at least, the operator health signal, determine if the operator fatigue score exceeds a warning threshold, and transmit the operator warning signal to the operator warning system if the operator fatigue score exceeds the warning threshold; and
   a braking system configured to reduce speed or halt motion of the locomotive as it moves along the track, and wherein the electronic controller is further configured to direct the braking system to reduce speed or halt motion of the locomotive as it moves along the track if the operator fatigue score exceeds a braking threshold.

2. The locomotive of claim 1, wherein the operator health monitor includes a wearable health monitor to be worn by the operator during operation of the locomotive.

3. The locomotive of claim 2, wherein the operator health monitor includes one or more of a heart rate monitor, a blood alcohol concentration monitor, a galvanic skin response sensor, a sweat analyzing sensor, and a blood pressure monitor.

4. The locomotive of claim 2, wherein the operator health signal includes one or more of heart rate information, blood alcohol concentration information, blood pressure information, and body temperature information.

5. The locomotive of claim 1, further comprising a visual sensor disposed within the operator cabin, operatively associated with the controller, and configured to generate a visual operator fatigue signal and wherein determining the operator fatigue score, by the electronic controller, is further based on the visual operator fatigue signal.

6. The locomotive of claim 5, wherein the controller is further configured to analyze the visual operator fatigue signal to determine one or more of operator motion, operator facial characteristics, and operator eye conditions and wherein determining the operator fatigue score, by the electronic controller, is further based on one or more of the operator motion, the operator facial characteristics, and the operator conditions.

7. The locomotive of claim 1, further comprising a motion sensor disposed within the operator cabin, operatively associated with the controller, and configured to generate an operator motion signal and wherein determining the operator fatigue score, by the electronic controller, is further based on the operator motion signal.

8. The locomotive of claim 7, wherein the controller is further configured to analyze the operator motion signal to determine if a lack of motion, by the operator, exists and wherein determining the operator fatigue score, by the electronic controller, is further based on whether or not the lack of motion, by the operator, exists.

9. The locomotive of claim 1, wherein the operator warning system includes one or more of an audio warning device, a visual warning device, and a vibratory warning device.

10. A system for monitoring fatigue of an operator of a locomotive, the locomotive including a car body having an operator cabin, the system comprising:
    an operator health monitor within the operator cabin, the operator health monitor configured to monitor at least one health condition associated with the operator and configured to generate an operator health signal associated with the at least one condition;
    an operator warning device configured to present the operator with an operator warning in response to an operator warning signal; and
    a controller operatively associated with, at least, the operator health monitor, the controller configured to receive the operator health signal, determine an operator fatigue score based on, at least, the operator health signal, determine if the operator fatigue score exceeds a warning threshold, and transmit the operator warning signal to the operator warning signal if the operator fatigue score exceeds the warning threshold,
    a braking system configured to reduce speed or halt motion of the locomotive as it moves along a track, and wherein the controller is further configured to direct the braking system to reduce speed or halt motion of the locomotive as it moves along the track if the operator fatigue score exceeds a braking threshold.

11. The system of claim 10, wherein the operator warning device is a visual warning device configured to present the operator with a visual warning in response to the operator warning signal.

12. The system of claim 10, wherein the operator warning device is an audio warning device configured to present the operator with an audio warning in response to the operator warning signal.

13. The system of claim 10, further comprising a wireless connectivity link and wherein the controller is further configured to transmit the operator fatigue score to an information center via the wireless connectivity link.

14. The system of claim 10, wherein the operator health monitor includes a wearable health monitor to be worn by the operator during operation of the locomotive the operator health signal includes one or more of heart rate information, blood alcohol concentration information, blood pressure information, and body temperature information.

15. A method for monitoring fatigue of an operator of a locomotive, the method comprising:

monitoring, by an operator health monitor within an operator cabin of the locomotive, at least one health condition of the operator;

generating, by the operator health monitor, an operator health signal associated with the at least one condition;

receiving, by an electronic controller, the operator health signal;

determining, by the electronic controller, an operator fatigue score based on, at least, the operator health signal;

determining, by the electronic controller, if the operator fatigue score exceeds a warning threshold;

presenting, using an operator warning device, the operator with an operator warning if the operator fatigue score exceeds the warning threshold; and decreasing speed of the locomotive, utilizing a braking system, if the operator fatigue score exceeds a braking threshold.

16. The method of claim 15, further comprising generating a visual operator fatigue signal, by a camera, and wherein determining the operator fatigue score is further based on the visual operator fatigue signal.

17. The method of claim 15, further comprising generating an operator motion signal, by a motion sensor, and wherein determining the operator fatigue score is further based on the operator motion signal.

* * * * *